United States Patent
Edidin et al.

(10) Patent No.: US 8,187,327 B2
(45) Date of Patent: May 29, 2012

(54) SELECTIVELY-EXPANDABLE BONE SCAFFOLD

(75) Inventors: Avram Allan Edidin, Sunnyvale, CA (US); Arthur E. Ferdinand, San Jose, CA (US); Cesar A. Ico, San Francisco, CA (US); Aaron D. Markworth, Saddle Brook, NJ (US)

(73) Assignee: Kyphon SARL, Neuchatel (CH)

( * ) Notice: Subject to any disclaimer, the term of this patent is extended or adjusted under 35 U.S.C. 154(b) by 1533 days.

(21) Appl. No.: 11/131,345

(22) Filed: May 18, 2005

(65) Prior Publication Data

US 2006/0264945 A1 Nov. 23, 2006

(51) Int. Cl.
*A61F 2/44* (2006.01)

(52) U.S. Cl. .................. 623/17.11; 606/86 R (58) Field of Classification Search .............. 606/62–63, 606/86 R; 623/1.11–1.2, 17.11–17.16
See application file for complete search history.

(56) References Cited

U.S. PATENT DOCUMENTS

| | | | |
|---|---|---|---|
| 4,083,369 A | 4/1978 | Sinnreich | |
| 4,313,434 A | 2/1982 | Segal | |
| 4,327,736 A | 5/1982 | Inoue | |
| 4,733,665 A | 3/1988 | Palmaz | |
| 4,739,762 A * | 4/1988 | Palmaz | 623/1.11 |
| 4,776,337 A | 10/1988 | Palmaz | |
| 4,793,348 A | 12/1988 | Palmaz | |
| 4,969,888 A | 11/1990 | Scholten et al. | |
| 5,102,417 A | 4/1992 | Palmaz | |
| 5,108,404 A | 4/1992 | Scholten et al. | |
| 5,211,259 A | 5/1993 | Kishi | |
| 5,254,091 A | 10/1993 | Aliahmad | |
| 5,316,023 A | 5/1994 | Palmaz et al. | |
| 5,360,443 A | 11/1994 | Barone et al. | |
| 5,382,261 A | 1/1995 | Palmaz | |
| 5,439,447 A | 8/1995 | Miraki | |
| 5,522,880 A | 6/1996 | Barone et al. | |
| 5,549,679 A * | 8/1996 | Kuslich | 623/17.12 |
| 5,571,170 A | 11/1996 | Palmaz et al. | |
| 5,571,171 A | 11/1996 | Barone et al. | |
| 5,578,072 A | 11/1996 | Barone et al. | |

(Continued)

FOREIGN PATENT DOCUMENTS

JP 8038618 2/1996

(Continued)

OTHER PUBLICATIONS

International Search Report for PCT/US06/18984 dated Mar. 2, 2007.

(Continued)

*Primary Examiner* — Nicholas Woodall (57) ABSTRACT

An apparatus includes a scaffold configured to be disposed in a bone. The scaffold is configured to move from a first configuration to a second configuration. The scaffold in the second configuration is expanded from the first configuration. A selectively-expandable actuator is configured to be removably disposed within the scaffold. The selectively-expandable actuator is configured to move at least a portion of the scaffold to the second configuration when the selectively-expandable actuator is moved to an expanded configuration. A shape of the selectively-expandable actuator is substantially the same as a shape of the scaffold when the selectively-expandable actuator and the scaffold are in the second configuration. The selectively-expandable actuator configured to be removed from the scaffold when in a collapsed configuration. The scaffold is configured to remain substantially in the second configuration after the scaffold has been expanded by the actuator.

15 Claims, 8 Drawing Sheets

U.S. PATENT DOCUMENTS

| | | | |
|---|---|---|---|
| 5,656,036 A | 8/1997 | Palmaz | |
| 5,683,452 A | 11/1997 | Barone et al. | |
| 5,683,453 A | 11/1997 | Palmaz | |
| 6,127,597 A * | 10/2000 | Beyar et al. | 606/86 R |
| 6,190,404 B1 | 2/2001 | Palmaz et al. | |
| 6,241,734 B1 | 6/2001 | Scribner et al. | |
| 6,261,289 B1 * | 7/2001 | Levy | 606/63 |
| 6,379,383 B1 | 4/2002 | Palmaz et al. | |
| 6,423,083 B2 | 7/2002 | Reiley et al. | |
| 6,537,310 B1 | 3/2003 | Palmaz et al. | |
| RE38,146 E | 6/2003 | Palmaz et al. | |
| 6,582,467 B1 * | 6/2003 | Teitelbaum et al. | 623/17.11 |
| 6,716,216 B1 | 4/2004 | Boucher et al. | |
| 6,733,513 B2 | 5/2004 | Boyle et al. | |
| 6,736,843 B1 | 5/2004 | Fariabi | |
| 6,820,676 B2 | 11/2004 | Palmaz et al. | |
| 7,507,241 B2 * | 3/2009 | Levy et al. | 606/60 |
| 2003/0028246 A1 * | 2/2003 | Palmaz et al. | 623/1.49 |
| 2003/0088249 A1 * | 5/2003 | Furderer | 606/61 |
| 2003/0212426 A1 * | 11/2003 | Olson et al. | 606/191 |
| 2004/0133280 A1 * | 7/2004 | Trieu | 623/17.16 |
| 2004/0167625 A1 * | 8/2004 | Beyar et al. | 623/11.11 |
| 2005/0143827 A1 * | 6/2005 | Globerman et al. | 623/17.16 |

FOREIGN PATENT DOCUMENTS

WO  9856301  12/1998

OTHER PUBLICATIONS

The Gray Sheet, "Stent Inventors Swap Design Tips: Struts, Surfaces Continue to Evolve", Oct. 18, 2004, p. 17.

* cited by examiner

SELECTIVELY-EXPANDABLE BONE SCAFFOLD

BACKGROUND

The invention relates generally to expandable devices that can be inserted into a bone. More specifically, the invention relates to selectively-expandable bone scaffolds.

Small-tissue-insertion and -deployment tools allow access to the targeted tissue site through some minimally invasive procedures. When deployed within the targeted tissue site, such tools can assume enlarged, durable shapes. This allows cortical bone to be displaced in a desired manner and/or cavities to be created in cancellous bone without over-expansion, puncture, and/or abrasion of the structure. The tool can be left within the bone to provide additional support for the bone after expansion of the tool.

These known expandable tools can, for example, compact cancellous bone to fix a fracture, or to improve other osteoporotic and non-osteoporotic conditions of human and animal bones. These known devices, however, either lack sufficient directional control or fail to provide consistent compaction or distraction of the bone structure due to gaps in the structure of the tool.

Thus, a need exists for improvements in selectively-expandable structures that are disposable in bones.

SUMMARY OF THE INVENTION

An apparatus includes a scaffold configured to be disposed in a tissue (e.g., a bone, a vertebral bone, an intervertebral disc, etc.). The scaffold is configured to move from a first configuration to a second configuration. The scaffold in the second configuration is expanded from the first configuration. A selectively-expandable actuator is configured to be removably disposed within the scaffold. The selectively-expandable actuator is configured to move at least a portion of the scaffold to the second configuration when the selectively-expandable actuator is moved to an expanded configuration. A shape of the selectively-expandable actuator is substantially the same as a shape of the scaffold when the selectively-expandable actuator is in the expanded configuration and the scaffold is in the second configuration. The selectively-expandable actuator is configured to be removed from the scaffold when the selectively-expandable actuator is in a collapsed configuration. The scaffold is configured to remain substantially in the second configuration after the scaffold has been expanded by the actuator.

DETAILED DESCRIPTION

An apparatus includes a scaffold configured to be disposed in a tissue (e.g., a bone, a vertebral bone, an intervertebral disc, etc.). The scaffold is configured to move from a first configuration to a second configuration. The scaffold in the second configuration is expanded from the first configuration. A selectively-expandable actuator is configured to be removably disposed within the scaffold. The selectively-expandable actuator is configured to move at least a portion of the scaffold to the second configuration when the selectively-expandable actuator is moved to an expanded configuration. A shape of the selectively-expandable actuator is substantially the same as a shape of the scaffold when the selectively-expandable actuator is in the expanded configuration and the scaffold is in the second configuration. The selectively-expandable actuator is configured to be removed from the scaffold when the selectively-expandable actuator is in a collapsed configuration. The scaffold is configured to remain substantially in the second configuration after the scaffold has been expanded by the actuator.

The scaffold is configured to plastically deform when moved to the expanded configuration. Once the scaffold is deformed, its position is maintained within the body where positioned (i.e., a bone). Plastic deformation refers to a permanent change in shape and/or size of a material without fracture, produced by a stress sustained for a period of time beyond the elastic limit of the material.

The term "scaffold" is used herein to mean a deployable device that is configured to be disposed within a bone, such as a vertebra. The scaffold can optionally move a portion of the bodily structure in which it is disposed (e.g., cancellous bone within a vertebra). Regardless of whether the scaffold changed the position of the bodily structure upon deployment, the scaffold can maintain, or assist in maintaining, the shape and/or position of the bodily structure.

The scaffold is configured to remain substantially in its second configuration after the selectively-expandable actuator has been removed. The term "substantially" in this context refers to the fact that the scaffold may possibly undergo some insignificant amount of compression (e.g., change in shape and/or position) while remaining in the bone.

The term "selectively-expandable actuator" is used herein to mean an actuator that can be expanded and collapsed periodically for a period of time and/or randomly. Additionally, the actuator can be expanded intermittently and/or through varying degrees of expansion and collapsing. For example, the actuator need not be completely expanded or completely collapsed.

Figure 1:
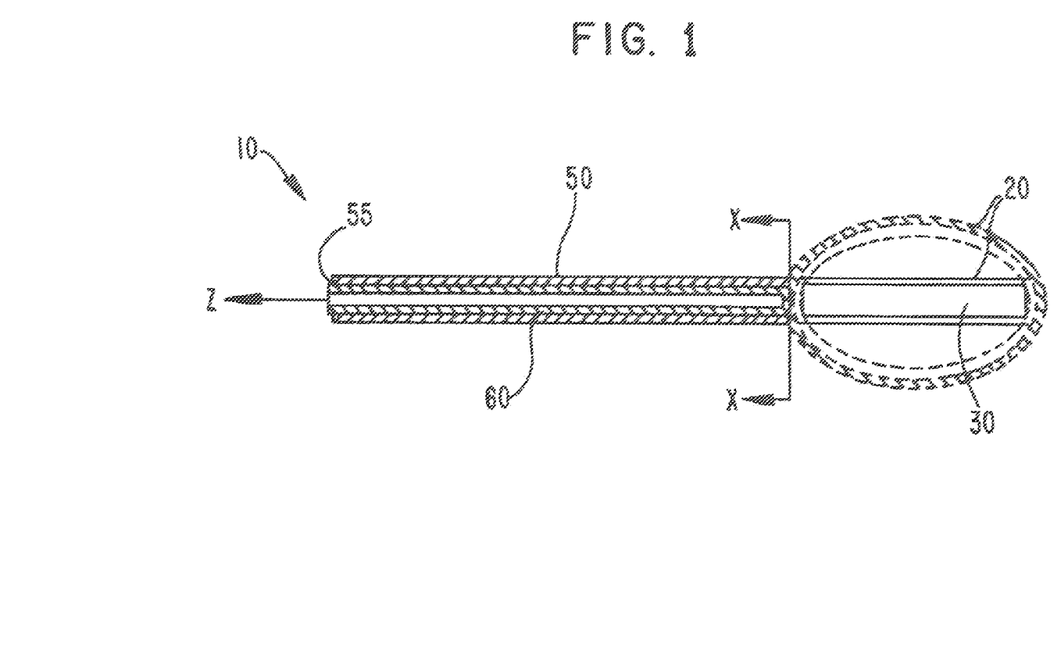
FIG. 1 is a schematic cross-sectional view of a medical device according to an embodiment of the invention.

FIG. 1 is a schematic cross-sectional view of a medical device 10 according to an embodiment of the invention. The medical device includes a scaffold 20 that is configured to be disposed in a bone (not illustrated). The scaffold 20 is configured to move between a first configuration illustrated as a solid line in FIG. 1 and a second configuration illustrated as a dashed line in FIG. 1. The scaffold 20 is collapsed in the first configuration and is expanded in the second configuration.

A selectively-expandable actuator 30 is configured to be removably disposed within the scaffold 20. The selectively-expandable actuator 30 is configured to move at least a portion of the scaffold 20 to the second configuration when the selectively-expandable actuator 30 is moved to its expanded configuration.

A shape of the selectively-expandable actuator 30 is substantially the same as a shape of the scaffold 20 when the selectively-expandable actuator 30 is in the expanded configuration and the scaffold 20 is in the second configuration. Additionally, the selectively-expandable actuator 30 and the scaffold 20 can be concentrically and/or coaxially aligned.

After the selectively-expandable actuator 30 has moved the scaffold 20 to the second configuration, the selectively-expandable actuator 30 can be returned to its collapsed configuration and removed from the scaffold 20. The scaffold 20 is configured to remain substantially in the second configuration within the bone after the selectively-expandable actuator 30 has been removed. The selectively-expandable actuator 30 need only be collapsed a sufficient degree to be removed from the scaffold 20. In other words, the collapsed configuration is any configuration that allows the selectively-expandable actuator 30 to be inserted into and/or removed from the scaffold 20.

The scaffold 20 can be inserted into a body percutaneously and is inserted through the bone when the scaffold 20 is in the first configuration. After the scaffold 20 is moved to the second configuration, the scaffold 20 remains within the bone.

The scaffold 20 is plastically deformed when moved into the second configuration. In other words, the mechanical properties of the scaffold 20 change such that the scaffold 20 can not return to its initial configuration. The geometry of the scaffold 20 is permanently altered.

When the scaffold 20 is expanded (i.e., moved to its second configuration) in a vertebra, the scaffold 20 is configured to expand a volume in the cancellous bone of the vertebra. The volume can be created, for example, by compacting the cancellous bone and/or moving, and subsequently extracting, the cancellous bone or other biological material. The medical device 10 is able to compact bone by providing a force across the scaffold 20 while the scaffold is actuated. The scaffold 20 is moved apart by the expandable actuator 30.

In some embodiments, the selectively-expandable actuator 30 includes a balloon. The balloon can be either symmetrical or asymmetrical about a longitudinal axis of the balloon. The balloon is configured to be expanded, for example, by a liquid and/or a gas.

The medical device 10 includes a shaft 50, which is coupled to the scaffold 20. The shaft 50 is configured to be moved in the direction away from the scaffold 20 indicated by arrows X-X in FIG. 1. The shaft 50 is used to insert the medical device 10 into the bone and is removed after expansion of the scaffold 20 to the second configuration. In some embodiments, shaft 50 can be a cannula defining a passageway or working channel 55.

The scaffold 20 can be removably coupled to the shaft 50. Prior to deployment of the scaffold 20, the shaft 50 can be used as a filler tube. Filler material can be injected through the interstices of the scaffold 20 for placement within the vertebra (e.g., adjacent to the cancellous bone). The working channel 55 of the shaft 50 can also be used as a passageway for the use of additional working tools.

Shaft 60 that is configured to be removably inserted within passageway 55 defined by shaft 50. To remove the selectively-expandable actuator 30 from within the scaffold 20, shaft 60 can be withdrawn from the medical device 10 in the direction illustrated by arrow Z.

Figure 2A:
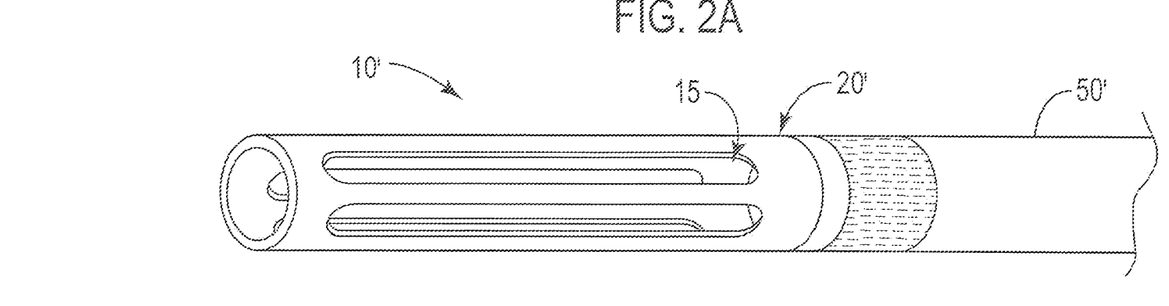
FIGS. 2*a* and 2*b* are perspective views of a bone scaffold according to an embodiment of the invention.
Figure 2B:
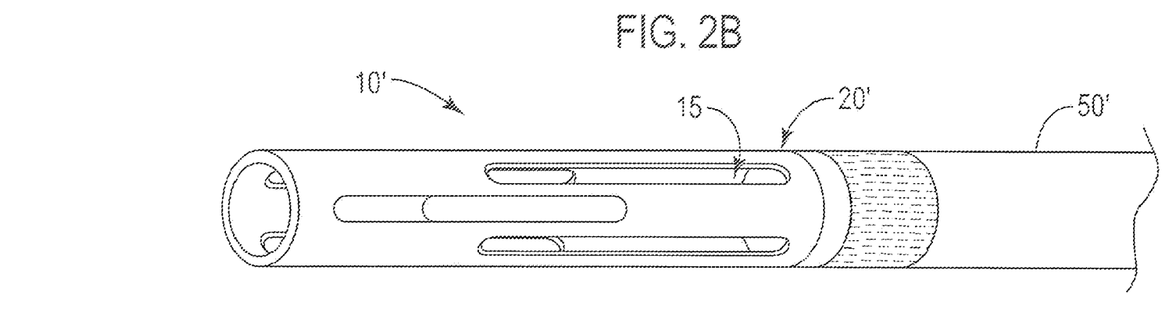

FIGS. 2a and 2b are perspective views of a medical device 10' including a bone scaffold 20' according to an embodiment of the invention. As illustrated in FIG. 2, the scaffold 20' includes multiple oval shaped slots 15 along its length. The shape of each slot 15 affects the shape of the scaffold 20' when the scaffold 20' is in the expanded configuration. The slots 15 can be either symmetrical or asymmetrical about the circumference of the scaffold 20'. As the actuator (not shown in FIG. 2a or 2b) expands, the scaffold 20' expands within the bone. In some embodiments, the scaffold 20' and actuator (not shown) compact cancellous bone as the scaffold and the actuator move to their respective expanded configurations.

The scaffold 20' is removably coupled to a shaft 50' which can be used as, for example, a cannula. Once the scaffold 20' is expanded, the shaft 50', is removed from the scaffold 20', leaving the scaffold 20' in the bone.

Figure 3:
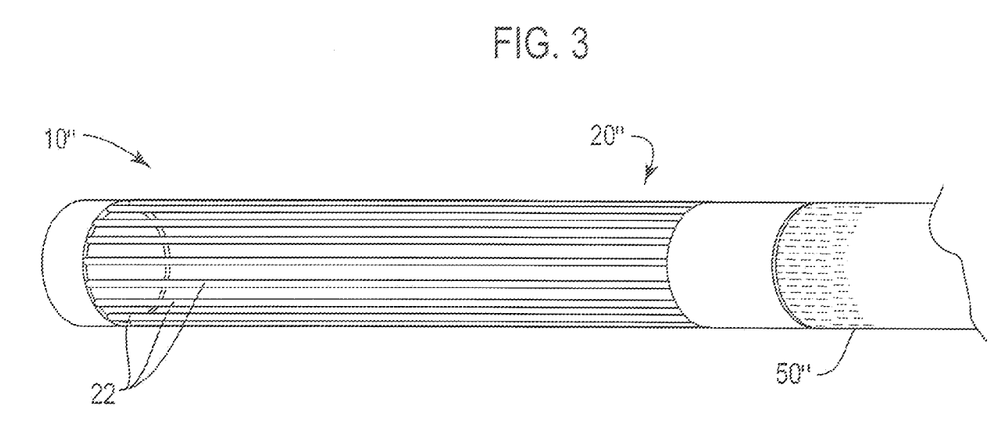
FIG. 3 is a perspective view of a bone scaffold according to another embodiment of the invention.

FIG. 3 is a perspective view of a medical device 10" including a bone scaffold 20", and an associated shaft 50", according to a further embodiment of the invention. The scaffold 20" includes multiple wires 22 disposed about the circumference of scaffold 20". In some embodiments, the wires 22 are expanded into cancellous bone of a vertebra by an actuator, such as, for example, a balloon actuator. The scaffold 20" can then be moved (e.g., rotationally and/or laterally) such that the wires cut the cancellous bone and the cancellous bone is removed, thereby modifying a volume in the vertebra created by medical device 10".

Figure 4:
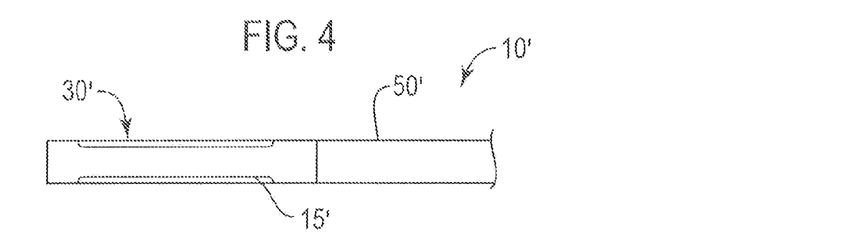
FIG. 4 is a side view of a medical device according to the invention in a first configuration.
Figure 5A:
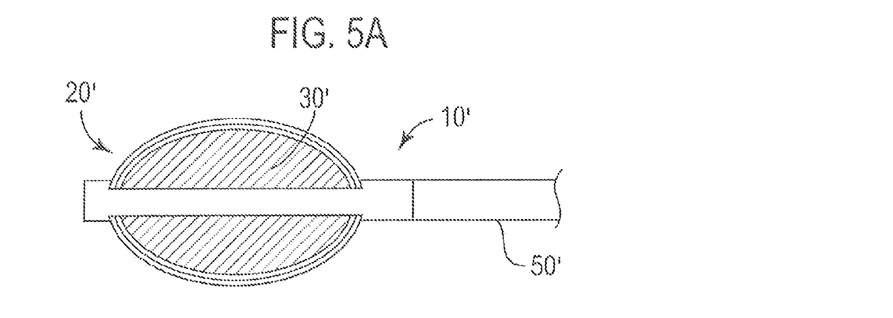
FIGS. 5*a* and 5*b* are side views of a medical device according to the invention in a second configuration with an actuator disposed within a scaffold.
Figure 5B:
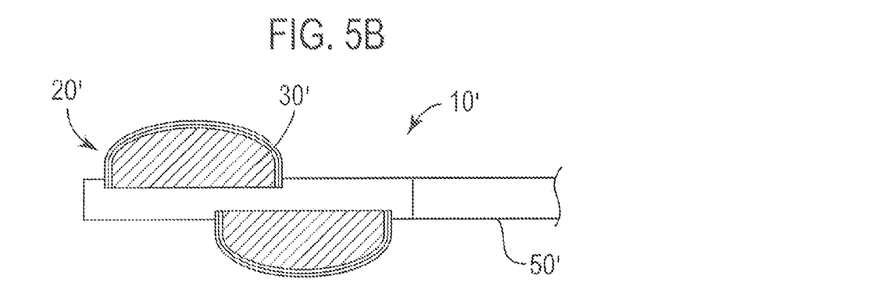
Figure 6:
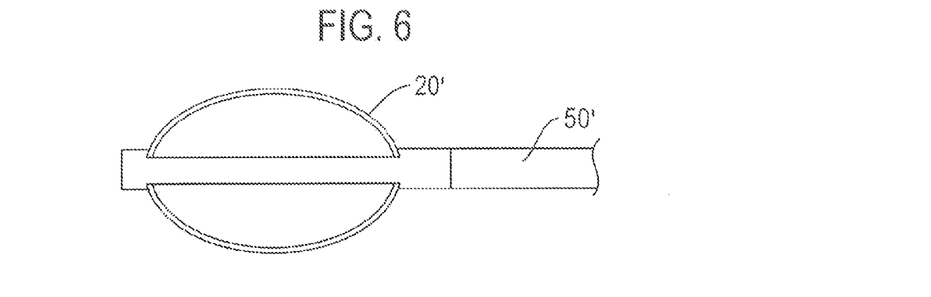
FIG. 6 is a side view of a medical device according to the invention in a second configuration with no actuator disposed within the scaffold.

FIGS. 4-6 illustrate a side view of the medical device 10' of FIG. 2 in various configurations. FIG. 4 is a side view of medical device 10' in the first configuration. As discussed above, the medical device 10' is in its first configuration prior to being inserted into a bone, such as a vertebra. In some embodiments, the selectively-expandable actuator 30' is disposed within the scaffold 20' when inserted into the bone, the scaffold 20' having multiple slots 15' formed along its length as shown in FIG. 4. In other embodiments, the scaffold 20' can be inserted into the bone first and then the selectively-expandable actuator 30' can be inserted through the passageway defined by shaft 50' and into an interior of scaffold 20'.

FIGS. 5a and 5b are side views of medical device 10' in the second configuration with the selectively-expandable actuator 30' disposed within the scaffold 20'. As the selectively-expandable actuator 30' expands the scaffold 20', a volume is defined within the cancellous bone disposed about medical device 10'. In some embodiments, the cancellous bone is compacted by the actuator 30' and the scaffold 20'.

FIG. 6 is a side view of the apparatus 10' in its second configuration after the selectively-expandable actuator 30' has been removed from the scaffold 20'. Once the selectively-expandable actuator 30' has been removed from the scaffold 20', the shaft 50' is removed from the scaffold 20', and the scaffold 20' remains in the bone.

The shaft 50' can be removably coupled to the scaffold 20' by known connectors. For example, the shaft 50' can be coupled to the scaffold 20' using a threaded connector, a break-away connector, a lock-and-key connection, etc. Any suitable connection device is appropriate, provided the shaft 50' can be removed from the scaffold 20' once the scaffold 20' is positioned and expanded in the bone.

Figure 7:
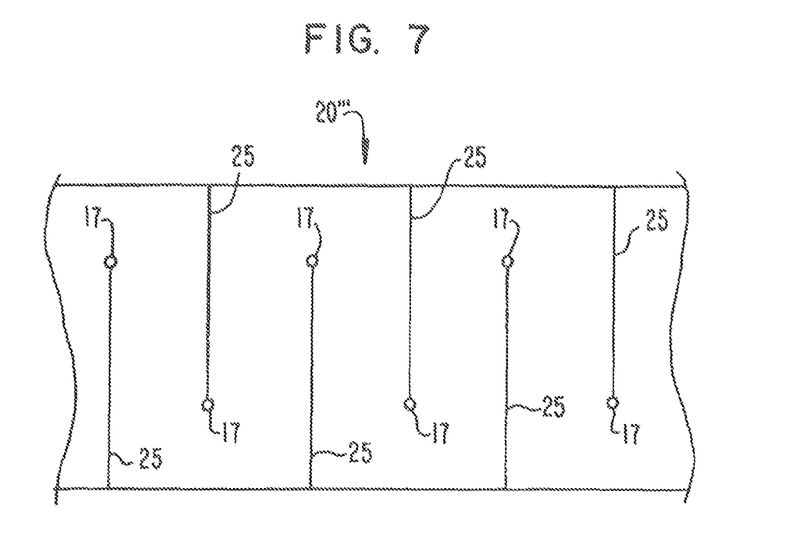
FIG. 7 is a side view of a portion of a scaffold according to another embodiment of the invention in a first configuration.
Figure 8:
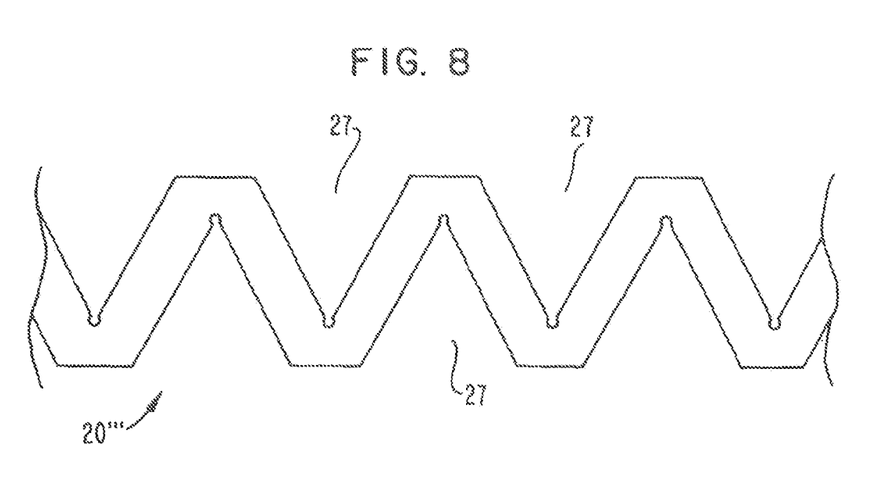
FIG. 8 is a side view of the portion of the scaffold illustrated in FIG. 7 in a second configuration.

FIG. 7 is a side view of a portion of a scaffold 20''' according to another embodiment of the invention when the scaffold 20''' is in its first configuration. FIG. 8 is a side view of the portion of the scaffold 20''' illustrated in FIG. 7 in its second configuration. In some embodiments, slits 25 are defined along the scaffold 20''' such that when scaffold 20''' is expanded by an actuator (not illustrated) as discussed above, scaffold 20''' moves to the second configuration illustrated in FIG. 8. In the second configuration, multiple gaps 27 are formed between adjacent portions of the scaffold 20'''.

As illustrated in FIG. 7, openings 17 are defined at an end of each slit 25. As the scaffold 20''' moves to the second configuration, the scaffold 20''' expands uniformly along its length. The longer the scaffold 20''', the greater the potential change in diameter within the stress limits of the material used to make the scaffold 20'''. For example, if a material can tolerate three degrees of separation at the openings 17, a longer scaffold 20''' would result in a larger diameter change for the same three degrees of tolerance.

In an alternative arrangement (not shown) multiple scaffolds 20''' can be oriented concentrically (i.e., one inside the other) with respect to one another. Additionally, the concentrically-oriented scaffolds 20''' can be rotated with respect to one another such that the slits 17 for one scaffold 20''' are out of phase (i.e., not completely overlapping) with the slits 17 for the other scaffold 20'''. In such a configuration, when the scaffolds 20''' are expanded, the size of the gaps 27 collectively are reduced and the strength of the scaffold combination (i.e., the inner scaffold 20''' and the outer scaffold 20''') is increased. The scaffolds 20''' can be welded in place to maintain their relative position.

When the scaffolds 20''' are oriented concentrically and then expanded, portions of the inner scaffold 20''' expand outwardly, while portions of the outer scaffold 20''' collapse inwardly. The adjacent portions of each scaffold 20''' substantially inhibit the remaining scaffold 20''' from collapsing under external pressure. Such scaffolds 20''' can be formed, for example, from shape-memory material that is inserted in a collapsed configuration and expanded after insertion into a vertebral body.

Figure 9:
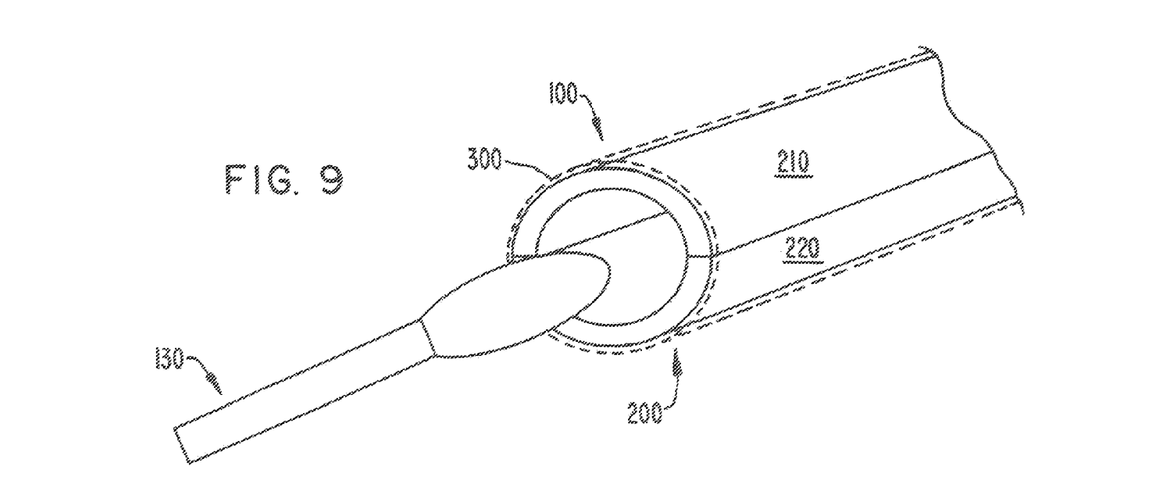
FIG. 9 is a perspective view of a medical device according to a further embodiment of the invention.
Figure 10:
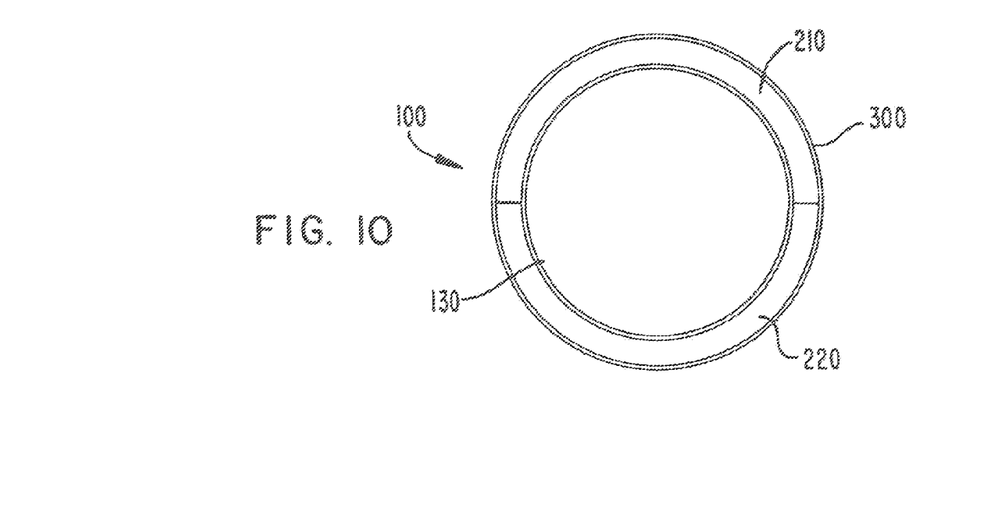
FIG. 10 is a front plan view of a portion of the medical device illustrated in FIG. 9 in a first configuration.
Figure 11:
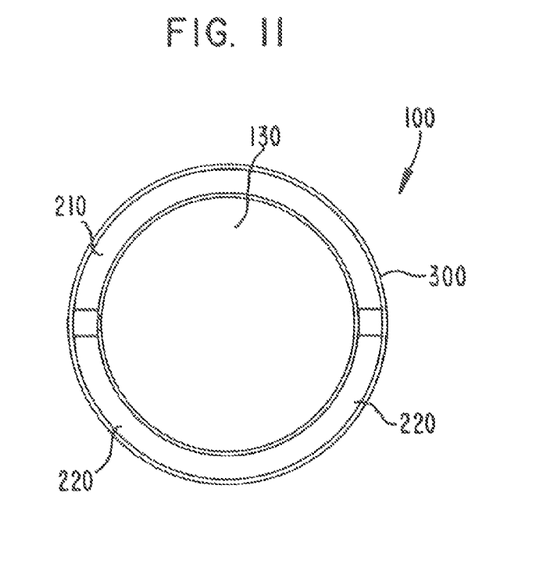
FIG. 11 is a front plan view of a portion of the medical device illustrated in FIG. 9 in a second configuration.

FIGS. 9-11 illustrate a medical device 100 that includes a scaffold 200 having a first portion 210 and a second portion 220 that are collectively movable between a first collapsed configuration (see FIG. 10) and a second expanded configuration (see FIG. 11). The first portion 210 and the second portion 220 are physically distinct. The first portion 210 is configured to contact the second portion 220 when the scaffold 200 is in its first configuration. When the scaffold 200 is moved to its second configuration, the first portion 210 is spaced apart from the second portion 220 as illustrated in FIG. 11.

An actuator 130 is removably coupled to the scaffold 200. The actuator 130 is configured to move the scaffold 200 from the first configuration to the second configuration. A sleeve 300 is disposed around the scaffold 200. The sleeve 300 is configured to bias the first portion 210 of the scaffold 200 towards the second portion 220 of the scaffold 200. In some embodiments, the sleeve is substantially elastic. When outward pressure of the actuator 130 is sufficient, the outward pressure can overcome the elasticity of the sleeve 300. The properties of the sleeve 300 may be varied such that the firs portion 210 of the scaffold 200 expands at a different rate than the second portion 220 of the scaffold 200 when actuated. In other words, the scaffold 200 can be expanded in an anisotropic manner.

Figure 12:
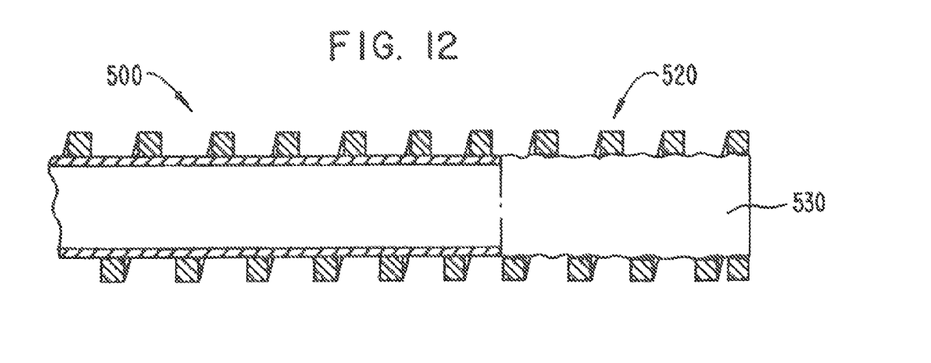
FIG. 12 is a side cross sectional view of a medical device according to an embodiment of the invention in a first configuration.
Figure 13:
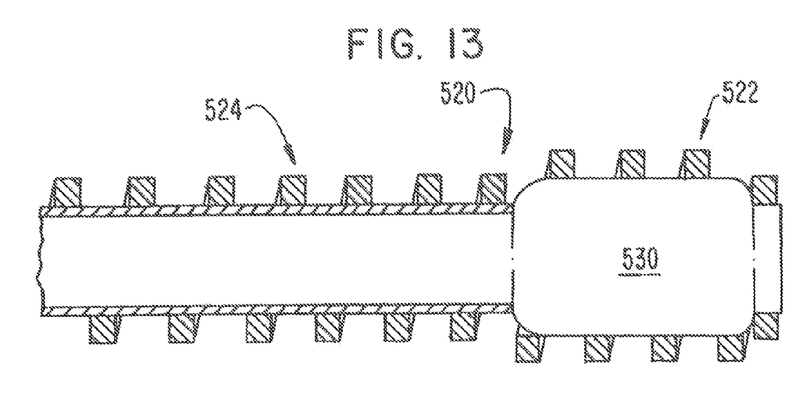
FIG. 13 is a side cross sectional view of a medical device according to an embodiment of the invention in a second configuration.
Figure 14:
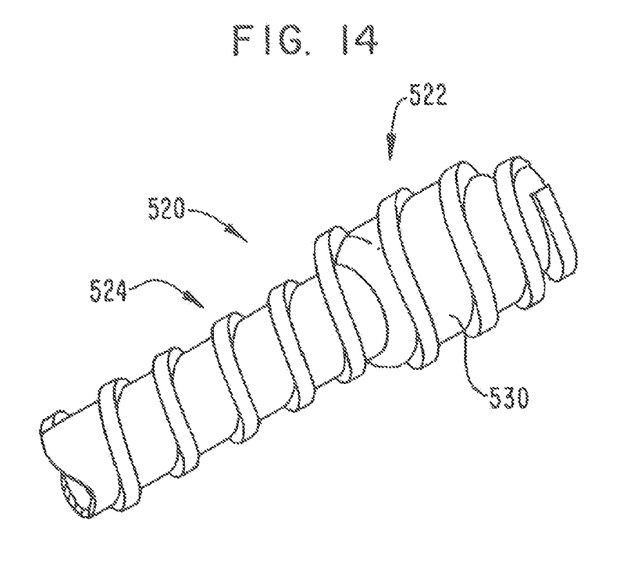
FIG. 14 is a perspective view of a medical device according to an embodiment of the invention in a second configuration.

Medical device 500, according to an embodiment of the invention is illustrated in FIGS. 12 through 14. FIG. 12 is a side cross-sectional view of the medical device 500 in its first configuration. FIG. 13 is a side cross-sectional view of the medical device 500 as illustrated on FIG. 12 in its second configuration. FIG. 14 is a perspective view of medical device 500 according to an embodiment of the invention in its second configuration.

As illustrated in FIGS. 12 through 14, the scaffold 520 has a substantially spiral shape. As illustrated in FIGS. 12 and 13, when the selectively-expandable actuator 530 is moved to its second configuration, only a portion 522 of the scaffold 520 that is contacted by the actuator 530 is moved to a second configuration and the portion 524 of the scaffold 520 not contacted by the actuator does not move to the second configuration.

The scaffold 520 can be either elastically or plastically deformed. Additionally, the selectively-expandable actuator 530 can be either uniformly expandable or non-uniformly expandable such that the shape of the scaffold 520 in its second configuration may vary along its length.

Conclusion

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

While the invention has been particularly shown and described with reference to embodiments thereof, it will be understood by those skilled in art that various changes in form and details may be made therein without departing from the spirit and scope of the invention.

For example, although the selectively-expandable actuators 30, 30', 130, 530 are described as including a single balloon, in alternative embodiments multiple independent actuators may be provided between within the scaffold. For example, the actuator(s) may include multiple chambers that are independently actuated to permit an isotropic deployment of the scaffold.

Although the scaffold is described without reference to specific materials, the scaffold can be made of any material sufficient to be inserted into body tissue and modify the volume of the tissue. For example, the scaffold can be made of Nitinol or stainless steel.

While the selectively-expandable actuator 30 is described above as being coupled to a separate shaft 60, in alternative embodiments the actuator 30 can be coupled to the same shaft 50 as the scaffold 20. In such a configuration, when the shaft 50 is uncoupled and removed from the scaffold 20, the actuator 30 would also be removed.

Additionally, although the selectively-expandable actuator 30 is primarily described as a balloon-type actuator, selectively-expandable actuator 30 can be any type of mechanical actuator configured to expand the scaffold 20 from within the scaffold 20. For example, the actuator can be a laterally expandable device including laterally extending projections that are configured to engage the scaffold 20 to move it to its expanded configuration. In other embodiments, the mechanical actuator can cause the expandable scaffold to be biased to have a substantially greater resistance to retrograde axial motion than to anterograde motion.

Although the scaffold 20 is described as being substantially cylindrical in the first configuration, in alternative embodiments, any shape sufficient to be modified to an expanded configuration to change the volume of tissue around the scaffold can be used. For example, the scaffold can be triangular, hexagonal, octagonal, etc.

Although removal of the actuator after expanding the scaffold is disclosed, in alternative embodiments, the actuator can remain in place within the scaffold, detach from the shaft to which it is attached and remain in the scaffold within the vertebra. In some embodiments, bone filler material may be inserted into the void created within the vertebra adjacent the scaffold.

Although described separately with respect to the various embodiments above, features of the disclosed embodiments may be interchangeably associated.

The invention claimed is:

1. An apparatus, comprising:
a scaffold configured to be disposed in a bone, the scaffold configured to move from a first configuration to a second configuration, the scaffold in the second configuration being expanded from the first configuration;
a shaft extending along a longitudinal axis with the scaffold removably coupled to and extending from a distal end of the shaft along the longitudinal axis, wherein in the first configuration the distal end of the shaft and the scaffold coupled to and extending from the distal end along the longitudinal axis have substantially similar outer diameters; and
a selectively-expandable actuator configured to be removably disposed within the scaffold through the shaft, the selectively-expandable actuator configured to move at least a portion of the scaffold to the second configuration when the selectively-expandable actuator is moved from a collapsed configuration to an expanded configuration, the selectively-expandable actuator configured to be removed from the scaffold when in the collapsed configuration, the entire shape of the selectively-expandable actuator being substantially the same as the entire shape of the scaffold when the selectively-expandable actuator is in the expanded configuration and the scaffold is in the second configuration, the entire shape of the selectively-expandable actuator being substantially the same as the entire shape of the scaffold when the selectively-expandable actuator is in the collapsed configuration and the scaffold is in the first configuration,
the scaffold configured to remain substantially in the second configuration after the scaffold has been expanded by the actuator.

2. The apparatus of claim 1, wherein the scaffold is plastically deformed in the second configuration.

3. The apparatus of claim 1, wherein the scaffold is configured to expand a volume within cancellous bone of a vertebra.

4. The apparatus of claim 1, wherein the scaffold defines a plurality of slots, a shape of each slot from the plurality of slots configured to determine a shape of the scaffold associated with the second configuration.

5. The apparatus of claim 1, wherein the scaffold defines a plurality of circumferentially disposed slots, a location of each slot from the plurality of circumferentially disposed slots being symmetrical about the scaffold, and
the selectively-expandable actuator includes an expandable balloon, the expandable balloon being symmetrically expandable.

6. The apparatus of claim 1, wherein the scaffold defines a plurality of circumferentially disposed slots, a location of each slot from the plurality of circumferentially disposed slots being asymmetrical about the scaffold, and
the selectively-expandable actuator includes an expandable balloon, the expandable balloon being symmetrically expandable.

7. The apparatus of claim 1, wherein the scaffold defines a plurality of circumferentially disposed slots, a location of each slot from the plurality of circumferentially disposed slots being asymmetrical about the scaffold, and
the selectively-expandable actuator includes an expandable balloon, the expandable balloon being asymmetrically expandable.

8. The apparatus of claim 1, wherein the scaffold defines a plurality of circumferentially disposed slots, a location of each slot from the plurality of circumferentially disposed slots being symmetrical about the scaffold, and
the selectively-expandable actuator includes an expandable balloon, the expandable balloon being asymmetrically expandable.

9. The apparatus of claim 1, wherein the selectively-expandable actuator is a balloon configured to be expanded using at least one of a gas and a liquid.

10. The apparatus of claim 1, wherein the scaffold includes a first semi-cylindrical portion and a second semi-cylindrical portion different from the first semi-cylindrical portion, the first semi-cylindrical portion configured to contact the second semi-cylindrical portion while the scaffold is in the first configuration, the first semi-cylindrical portion and the second semi-cylindrical portion configured to be spaced apart while the scaffold is in the second configuration.

11. The apparatus of claim 1, wherein the scaffold is configured to cut cancellous bone.

12. An apparatus, comprising:
a scaffold configured to be disposed in a bone, the scaffold configured to move from a first configuration to a second configuration, at least a portion of the scaffold in the second configuration being expanded from the first configuration, the scaffold being configured to expand a volume within cancellous bone of a vertebra;
a shaft extending along a longitudinal axis with the scaffold removably coupled to and extending from a distal end of the shaft along the longitudinal axis, wherein in the first configuration the distal end of the shaft and the scaffold coupled to and extending from the distal end along the longitudinal axis have substantially similar outer diameters; and
a selectively-expandable actuator configured to be removably disposed within the scaffold through the shaft, the selectively-expandable actuator configured to move at least a portion of the scaffold to the second configuration when the selectively-expandable actuator is moved from a collapsed configuration to an expanded configuration, the selectively-expandable actuator configured to be removed from the scaffold when the selectively-expandable actuator is in the collapsed configuration, the entire shape of the selectively-expandable actuator being substantially the same as the entire shape of the scaffold when the selectively-expandable actuator is in the expanded configuration and the scaffold is in the second configuration, the entire shape of the selectively-expandable actuator being substantially the same as the entire shape of the scaffold when the selectively-expandable actuator is in the collapsed configuration and the scaffold is in the first configuration,
the scaffold configured to remain substantially in the second configuration after the scaffold has been expanded by the actuator.

13. The apparatus of claim 12, wherein the scaffold is plastically deformed in the second configuration.

14. The apparatus of claim 12, wherein the actuator includes an expandable balloon, the expandable balloon being one of uniformly expandable and non-uniformly expandable.

15. The apparatus of claim 12, wherein the scaffold has a spiral configuration.

* * * * *